US010878010B2

(12) United States Patent
Labkoff et al.

(10) Patent No.: US 10,878,010 B2
(45) Date of Patent: Dec. 29, 2020

(54) SYSTEM AND METHOD FOR CLINICAL TRIAL CANDIDATE MATCHING

(71) Applicant: Intelligent Medical Objects, Inc., Northbrook, IL (US)

(72) Inventors: Steven E. Labkoff, Stamford, CT (US); Marc Perkowitz, Arlington Heights, IL (US); Fred E. Masarie, Jr., Husum, WA (US); Doris J. McGinness, Des Plaines, IL (US); Amy Y. Wang, Chicago, IL (US); Krishna Chaitanya Koyyalamudi, Wheeling, IL (US)

(73) Assignee: Intelligent Medical Objects, Inc., Rosemont, IL (US)

(*) Notice: Subject to any disclaimer, the term of this patent is extended or adjusted under 35 U.S.C. 154(b) by 678 days.

(21) Appl. No.: 14/886,963

(22) Filed: Oct. 19, 2015

(65) Prior Publication Data
US 2017/0109502 A1 Apr. 20, 2017

(51) Int. Cl.
*G06F 16/33* (2019.01)
*G16H 10/60* (2018.01)
*G16H 10/20* (2018.01)

(52) U.S. Cl.
CPC ......... *G06F 16/3341* (2019.01); *G16H 10/20* (2018.01); *G16H 10/60* (2018.01)

(58) Field of Classification Search
CPC .............................. G16H 10/20; G16H 50/70
USPC ......................................................... 705/2–4
See application file for complete search history.

(56) References Cited

U.S. PATENT DOCUMENTS

| 5,799,268 | A | 8/1998 | Boguraev |
| 5,930,788 | A | 7/1999 | Wical |
| 6,055,540 | A | 4/2000 | Snow et al. |
| 6,101,515 | A | 8/2000 | Wical et al. |
| 6,904,432 | B2 | 6/2005 | Charlot et al. |

(Continued)

FOREIGN PATENT DOCUMENTS

WO WO-2015127245 A1 * 8/2015 ............. G16H 10/60

OTHER PUBLICATIONS

"Semantic Web: Asking the Right Questions," Duch et al., Seventh International Conference on Information and Management Sciences, Urumchi, China, Aug. 12-19, 2008 entire document www.fizyka.umk.pl/ftp/pub/papers/kmk/08-SemWeb.pdf.

(Continued)

*Primary Examiner* — John P Go
(74) *Attorney, Agent, or Firm* — Quarles & Brady LLP; John Linzer

(57) ABSTRACT

A computer-implemented system and method for identifying potential clinical trial participants from one or more databases of patient electronic health information includes analyzing the clinical trial requirements and mapping those requirements to an interface terminology, where concepts of the interface terminology include a key concept and a group of one or more additional concepts that are related in the context of the clinical trial. The method further includes mapping the patient electronic health information to the interface terminology, building a query of one or more interface terminology elements; analyzing the patient health information for matches to the one or more interface terminology elements and, if necessary, iterating the process by adding additional interface terminology elements to the query.

15 Claims, 12 Drawing Sheets

(56) References Cited

U.S. PATENT DOCUMENTS

| | | |
|---|---|---|
| 7,167,858 B2 | 1/2007 | Naeymi-Rad et al. |
| 7,496,593 B2 | 2/2009 | Gardner et al. |
| 7,536,387 B2 | 5/2009 | Charlot et al. |
| 7,693,917 B2 | 4/2010 | Charlot et al. |
| 7,711,671 B2 | 5/2010 | Meyers |
| 7,870,117 B1 | 1/2011 | Rennison |
| 8,346,804 B2 | 1/2013 | Phillips |
| 2002/0128861 A1 | 9/2002 | Lau et al. |
| 2003/0179228 A1 | 9/2003 | Schreiber et al. |
| 2005/0240572 A1 | 10/2005 | Sung et al. |
| 2006/0069677 A1 | 3/2006 | Tanigawa et al. |
| 2006/0241974 A1* | 10/2006 | Chao ............... G06Q 10/00 705/2 |
| 2007/0005621 A1* | 1/2007 | Lesh ............... G16H 15/00 |
| 2007/0178501 A1* | 8/2007 | Rabinowitz ........ G16H 70/00 435/6.16 |
| 2007/0179776 A1 | 8/2007 | Segond et al. |
| 2008/0065452 A1 | 3/2008 | Naeymi-Rad et al. |
| 2008/0104032 A1 | 5/2008 | Sarkar |
| 2008/0306926 A1 | 12/2008 | Friedlander et al. |
| 2009/0083231 A1 | 3/2009 | Eberholst et al. |
| 2009/0254572 A1 | 10/2009 | Redlich et al. |
| 2010/0169299 A1 | 7/2010 | Pollara |
| 2010/0262659 A1 | 10/2010 | Christiansen et al. |
| 2011/0066425 A1 | 3/2011 | Hudgins et al. |
| 2011/0138050 A1 | 6/2011 | Dawson et al. |
| 2011/0184960 A1 | 7/2011 | Delpha et al. |
| 2012/0179696 A1 | 7/2012 | Charlot et al. |
| 2016/0019365 A1 | 1/2016 | Ober, Jr. |
| 2016/0063213 A1 | 3/2016 | Blue |
| 2016/0063214 A1 | 3/2016 | Blue |
| 2016/0098389 A1* | 4/2016 | Bruno ............... G06F 40/205 704/9 |

OTHER PUBLICATIONS

Virginia Tech SNOMED Core Structures 2nd AAHA Software Vendors Summit, Apr. 21, 2009.

"Social tagging overview (SharePoint Server 2010)" May 12, 2010 entire document http://technet.microsoft.com/en-us/library/ff608137.aspx.

Bronnert et al., Problem-Centered Care Delivery, Journal of AHIMA 83, No. 7 (Jul. 2012): 30-35.

* cited by examiner

Inclusion Criteria:

- Patient is at least 18 years old.
- Patient has been diagnosed with symptomatic MM with measurable disease that includes at least one of the following:

Serum M protein ≥1g/dl Urine M protein ≥ 200 mg/24 hrs Involved free light chain level ≥ 10 mg/dl and an abnormal serum free light chain ratio (<0.26 or >1.65).

- The patient is a candidate for systemic therapy that includes an IMiD® (e.g., lenalidomide, pomalidomide, thalidomide) and/or proteasome inhibitor (e.g., bortezomib, carfilzomib) as part of the initial regimen.
- No more than 30 days from baseline bone marrow evaluation as per this protocol to initiation of first-line therapy.
- Patient has read, understood and signed informed consent.

Exclusion Criteria:

- Patient is already receiving systemic therapy for MM (a single dose of bisphosphonates and up to 100 mg total dose of dexamethasone or equivalent corticosteroids are permitted prior to registration on study).
- Patient had another malignancy within the last 5 years (except for basal or squamous cell carcinoma, or in situ cancer of the cervix).

Patient is enrolled in a blinded clinical trial for the first-line treatment of multiple myeloma. Patients may be enrolled in subsequent clinical trials as long as continued access to data and tissue, as per this protocol, is not prohibited.

SYSTEM AND METHOD FOR CLINICAL TRIAL CANDIDATE MATCHING

BACKGROUND

1. Field of the Invention

The present application is direct to a method and system for identifying potential participants for one or more clinical trials.

2. Description of the Related Art

The drug development cycle is long, complex, and costly, although that process ideally is offset by the limited period of exclusivity that accompanies patent protection. Thus, as a rough approximation, a pharmaceutical company has a window of 20 years from the filing of a patent application on a substance with therapeutic potential to complete all R&D, including Phase 1, 2, and 3 clinical trials, secure FDA approval, release the product to market, and recoup its costs, before losing its exclusivity to generic drug manufacturers.

Clinical trials are necessary for several reasons, including establishing safety and efficacy and obtaining FDA approval. In order to find suitable trial participants, trial protocols are stored in one or more databases, e.g., in the database accessible from clinicaltrials.gov. The process of finding participants seems simple enough in theory; the database is reviewed to determine key inclusion and exclusion criteria so as to determined the scope of one or more trials, and then participants that possess the necessary inclusion criteria and do not possess the necessary exclusion criteria are located.

In practice, however, the process is considerably more complicated and drawn out, being rife with technological impediments. For example, within a database, the key inclusion and exclusion criteria are only a portion of the database contents for each trial, such that each trial may have extensive extraneous information that has little or no bearing on determining potential participant eligibility. Additionally, those inclusion and exclusion criteria often are recorded using free text, hampering attempts at retrieval and processing of that data.

In addition, recruiting patients for clinical trials is a major bottleneck in this process. Identification and recruitment of study participants is conducted in a haphazard fashion, often by contract research organizations (CROs) that support pharmaceutical companies in conducting trials and recruiting study participants. At one extreme, the burden of identifying participants is placed on potential participants themselves, e.g., by placing advertisements in public locations such as buses, trains, or on billboards requesting that individuals with one or more of the inclusion criteria contact a telephone number or visit a website for consideration in the trial. Such methods are inefficient at identifying potential trial participants and are limited in their reach. For example, an ideal candidate may not be identified in this manner if he or she does not use the bus or train that features the advertisement or pass by the location where a billboard is installed, or the potential candidate may not follow up and contact the CRO to determine qualification.

Many health organizations and clinicians are not directly connected with this process. As a result, there are difficulties and delays with finding adequate numbers of study subjects, and many patients who fit study criteria and could benefit from or support a trial are never matched to appropriate studies. As another result, the trials may experience significant delays in getting started, eating away at the duration of any ultimate exclusivity period.

In order to simplify the process, attempts have been made to automate aspects of the process, e.g., by employing natural language processing in order to retrieve the inclusion and exclusion criteria. These processes are not useful in identifying potential trial participants, however, such that considerable delays and expense still exist.

What are needed are a system and method that alleviate one or more of these drawbacks.

BRIEF SUMMARY

In one aspect, a method for identifying potential clinical trial participants may include the steps of: receiving, by a computer, a data file including data pertaining to a clinical trial, the data including at least one inclusion criterion and at least one exclusion criterion; determining a key concept of an interface terminology pertaining to the data; identifying one or more reference terminology concepts relating to the key concept in the context of the clinical trial; mapping, using a computer, one or more interface terminology concepts to the one or more reference terminology concepts; and analyzing, using the computer, a database of patient electronic health record information for a match to the key concept.

In another aspect, a method for identifying potential clinical trial participants may include the steps of: receiving, by a computer, a data file including data pertaining to a clinical trial, the data including at least one inclusion criterion and at least one exclusion criterion; mapping, using a computer, one or more interface terminology concepts to each of the at least one inclusion criterion and the at least one exclusion criterion; determining a key concept of an interface terminology pertaining to the data; identifying one or more concepts of an interface terminology relating to the key concept in the context of the clinical trial; and analyzing, using the computer, a database of patient electronic health record information for a match to the key concept or the one or more interface terminology concepts relating to the key concept.

In still another aspect, a method for identifying potential clinical trial participants may include: receiving, by a computer, a data file including data pertaining to a clinical trial, the data including at least one inclusion criterion and at least one exclusion criterion; mapping, using a computer, one or more interface terminology concepts to each of the at least one inclusion criterion and the at least one exclusion criterion; mapping, using a computer, elements of a database of patient electronic health record information to one or more interface terminology elements; building a query of at least one of the at least one inclusion criterion and the at least one exclusion criterion; determining, by a computer, which elements of the interface terminology map to the at least one inclusion criterion and the at least one exclusion criterion; and analyzing, by the computer, the elements of the database of patient electronic health record information for a match to the determined elements of the interface terminology.

BRIEF DESCRIPTION OF THE SEVERAL VIEWS OF THE DRAWINGS

FIG. 3 is a depiction of the inclusion and exclusion criteria of a clinical trial, with relevant concepts highlighted, indicating the application of tags to an interface terminology.

FIG. 8 is a screenshot of one example of a user interface of a tool for carrying out a method of identifying potential clinical trial participants.

DETAILED DESCRIPTION

With reference to the accompanying figures, a system and method to improve the matching of clinical trials with research subjects includes retrieving electronic database records relating to one or more clinical trials, parsing out inclusion and exclusion criteria stored within each database record into a structured, computable format, and matching those criteria with patient data from electronic health records (EHRs), which also preferably have been tagged with a robust, searchable terminology. This approach operates within normal clinical workflow and increases efficiency, reducing the time needed for recruiting subjects, and locating patients who might otherwise not be found, ultimately decreasing the lag time before commencement of a trial and accurately identifying potential participants, thereby improving the quality of match of participants with trial criteria. As additional benefits, the present system and method also may increase the time for pharmaceutical R&D and help to recoup research costs.

Figure 1A:
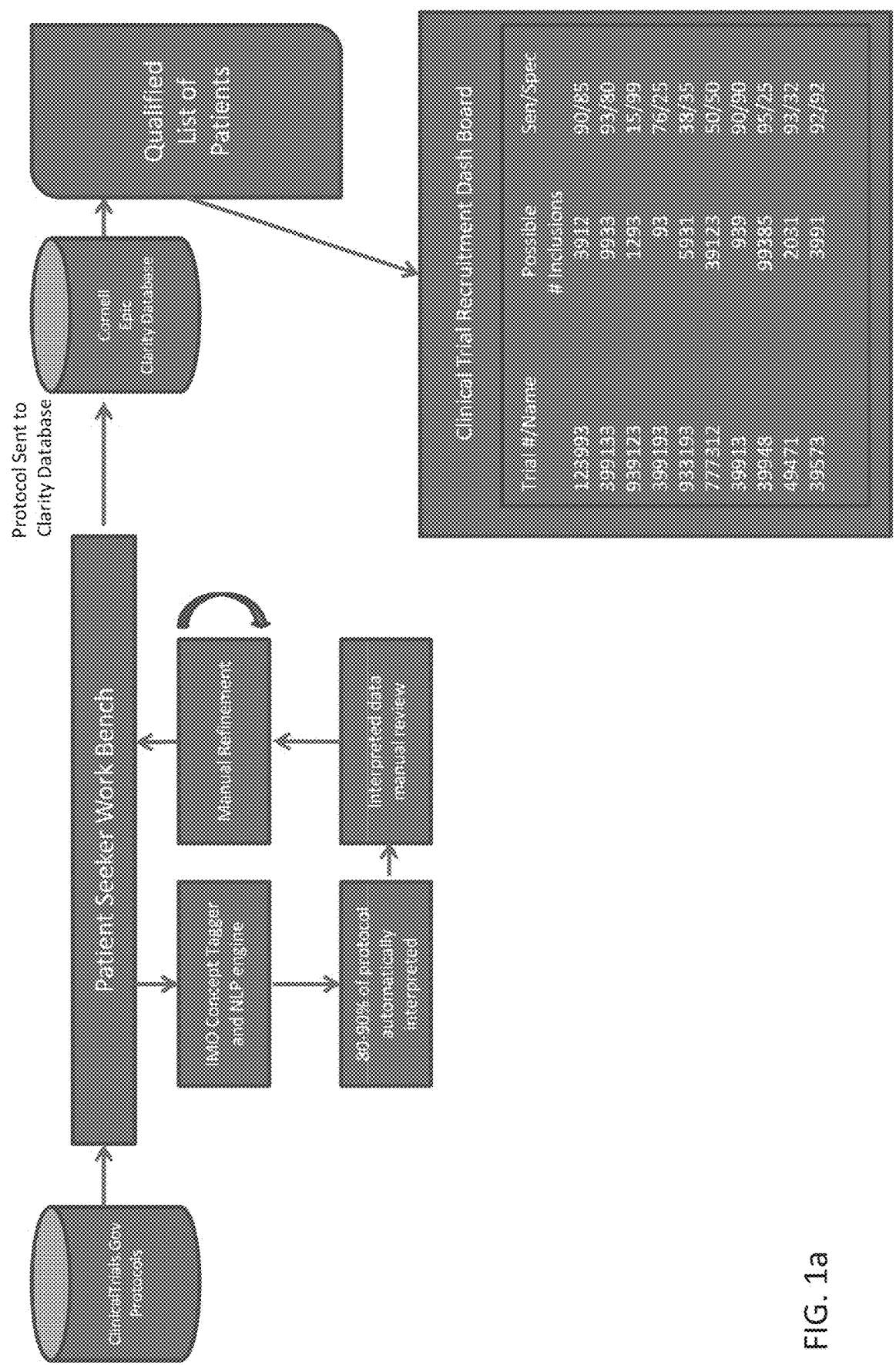
FIGS. 1a-1c are exemplary workflows of a method of identifying potential clinical trial participants.
Figure 1B:
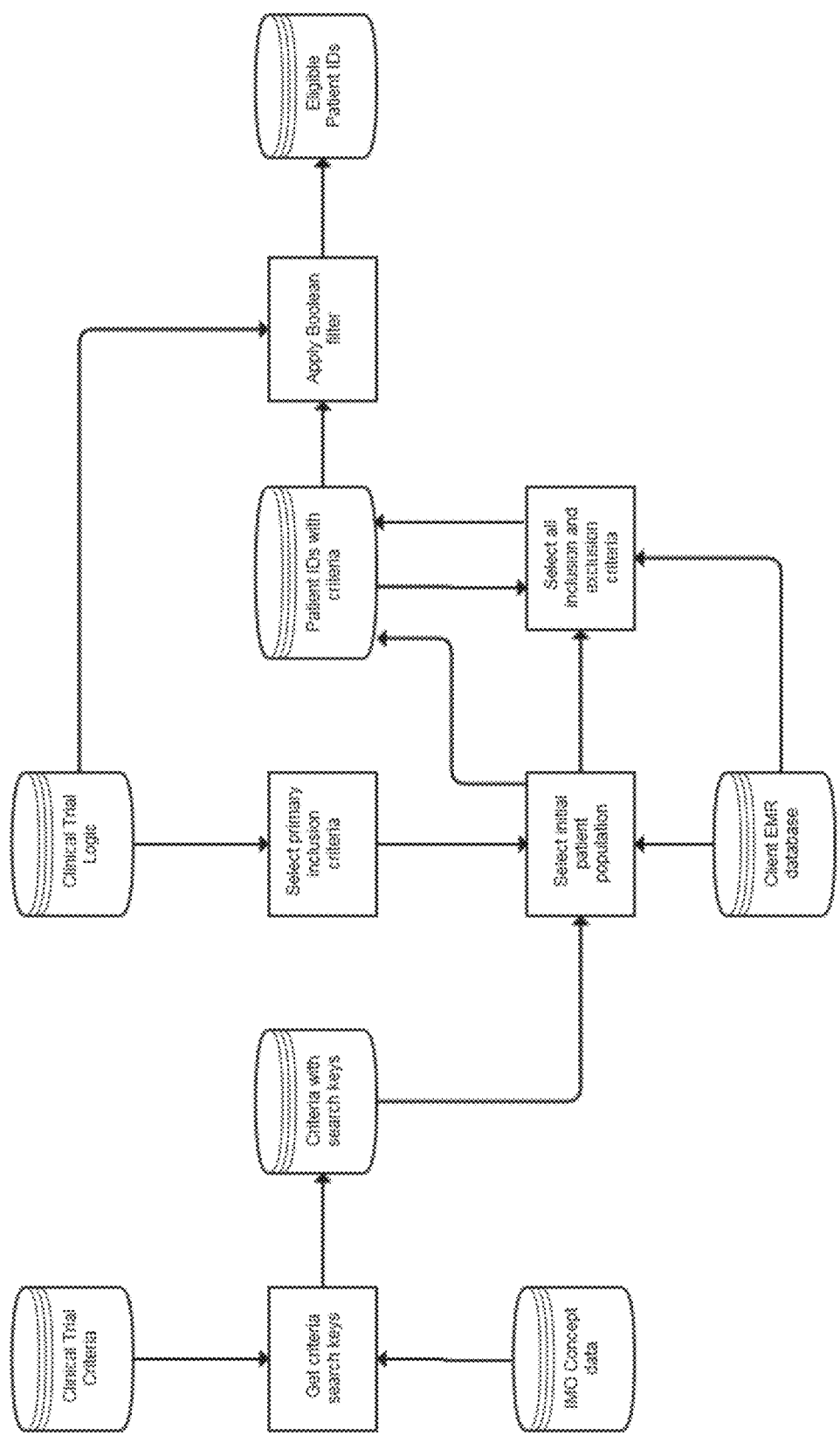
Figure 1C:
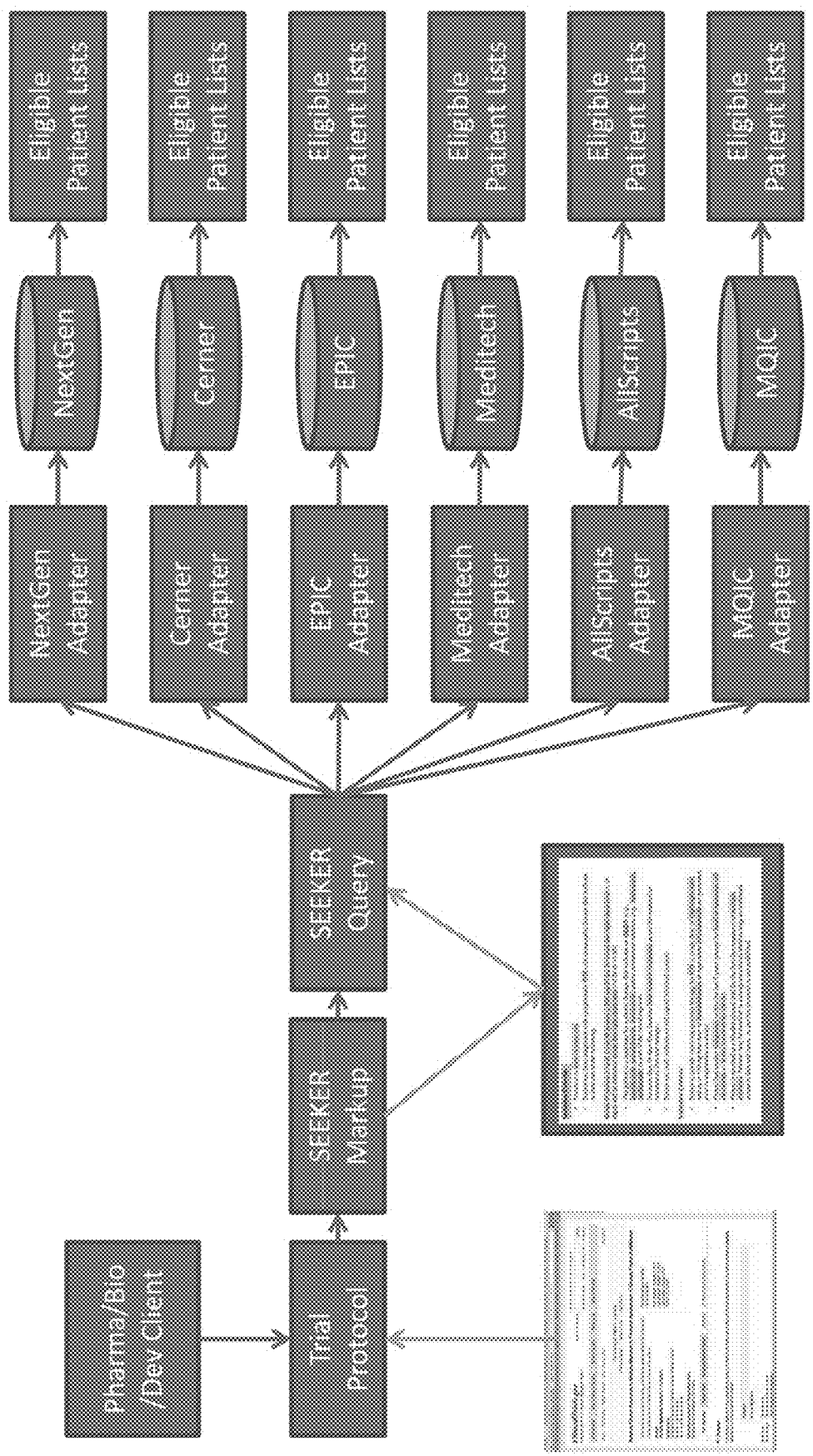

Two examples of the workflow may be shown in FIGS. 1a-c. As explained in greater detail below, the method may be parsed into two primary steps. First, trial and patient data may be normalized, i.e., structured and codified, in order to make it more readily searchable. Second, queries are built and executed in order to identify pools of potential trial participants.

Normalizing Patient Data—Analyzing Trial Parameters and Tagging Inclusion and Exclusion Criteria In one aspect, the method may involve storing data representing trial data in one or more databases. From these databases, the system may analyze and extract data representing inclusion and/or exclusion criteria and store that data in one or more database tables. The analyzing step may include scanning the database file for markers indicating the beginning and ending of each set of criteria. For example, a marker may be the presence of the word "criteria" followed within a predetermined number of words by the phrase "inclusion criteria" or "exclusion criteria." In another example, the marker may be the presence of the word "criteria" followed immediately by the phrase "inclusion criteria" or "exclusion criteria." In still another example, the data may be stored in a series of tables or otherwise compartmentalized within the database, and the system may point to the compartment storing the inclusion and/or exclusion criteria.

In addition to the formal inclusion and exclusion criteria as defined by the schema used to present trial information when requested by a user, the trial databases may include data corresponding to other potentially relevant information for matching trials to potential candidates. For example, each trial may include other eligibility criteria such as age values and/or ranges, gender restrictions, etc. Similarly, the trial data may include information corresponding to a geographic location for the trial. The system may be configured to analyze more than just the inclusion and exclusion criteria portions of each database entry, e.g., analyzing all data contained within each entry, to determine whether any additional data may be useful as part of the matching process.

Figure 2:
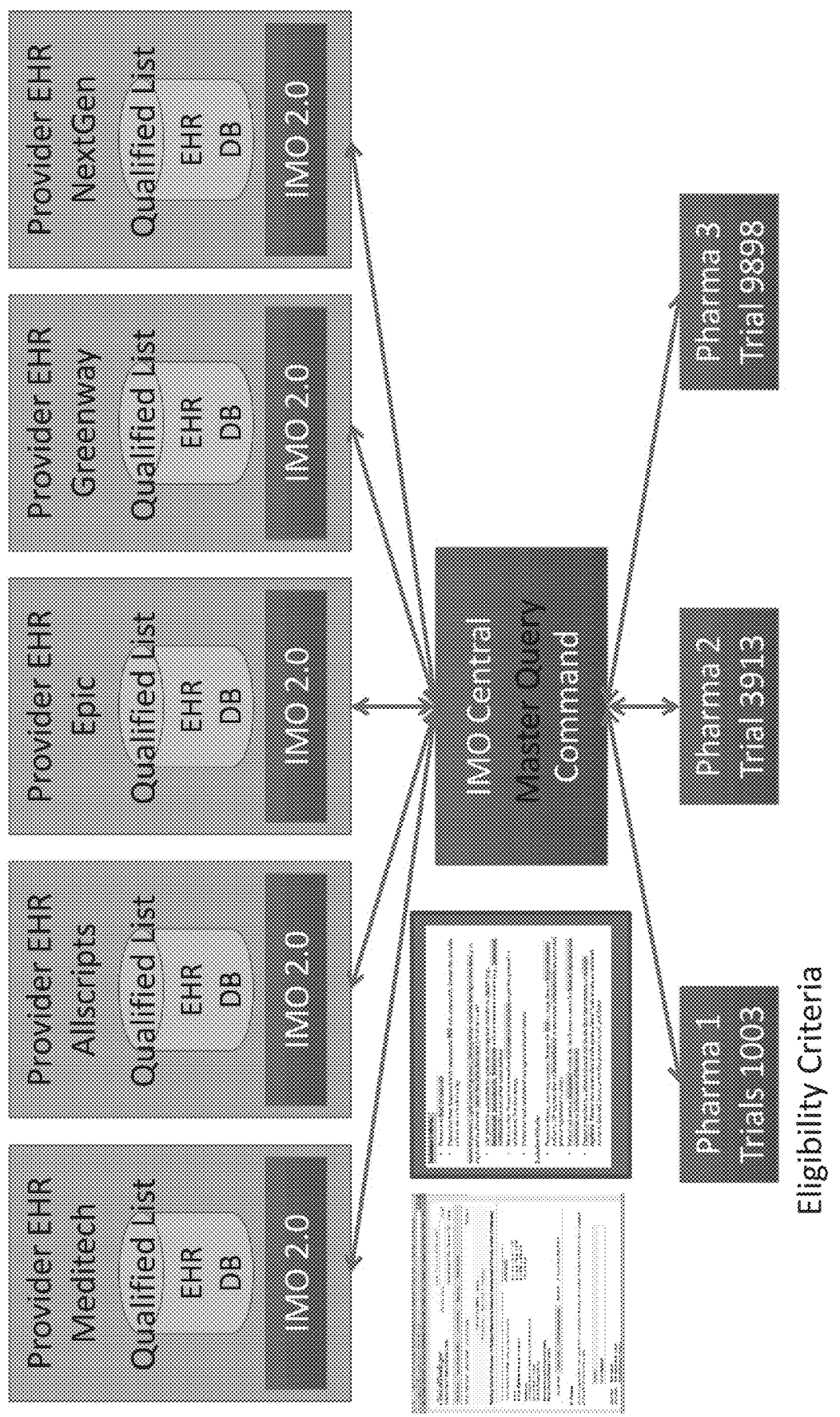
FIG. 2 is a depiction of a process for receiving electronic health record data from a plurality of databases at a plurality of institutions in order to analyze a plurality of clinical trial requests.

Patient data also may be stored in one or more separate database tables, which data may be used to build patient records within an electronic health record ("EHR") or within multiple, separate EHRs. In one example, patient data may be stored in multiple databases, such as when the system receives data reflecting multiple EHRs from multiple institutions, as seen in FIG. 2. Within an institution, patient data further may be stored in one or more databases. In the latter case, elements in multiple databases may be configured to correspond to a single patient, e.g., through the use of one or more pointers/flags.

Structuring and codifying of eligibility criteria and/or patient data may be automated, manual, or some combination thereof. One method of structuring and codifying the data may include mapping it to an interface terminology comprising a plurality of concepts within one or more domains and linking one or more descriptions (lexicals) to each concept, where each description reflects an alternative way to express the concept. Aspects of this mapping may be found in one or both of the commonly owned U.S. patent publication 2012/0179696, published Jul. 12, 2012, and U.S. patent publication 2014/0122117, published May 1, 2014, the contents of both of which are incorporated by reference in their entirety.

Elements of the interface terminology also may be mapped to one or more external codes sets, including, e.g.: administrative code sets that may be designed to support administrative functions of healthcare, such as reimbursement and other secondary data aggregation; clinical code sets that encode specific clinical entities involved in clinical work flow and allow for meaningful electronic exchange and aggregation of clinical data for better patient care; and reference terminology code sets that may be considered a "concept-based, controlled medical terminology" to maintain a common reference point in the healthcare industry. Reference terminologies also identify relationships between their concepts, e.g., relationships can be hierarchically defined, such as a parent/child relationship. Common examples of administrative code sets are the International Classification of Disease (ICD) and the Current Procedural Terminology, which is referred to via the trademark CPT. Examples of clinical code sets are LOINC and RxNorm. One example of a reference terminology is The Systematized Nomenclature of Medicine Clinical Terms, referred to under the trademark "SNOMED CT."

As seen in FIG. 3 with regard to clinical trial information, one example of extracting relevant data is shown. In this example, the inclusion and exclusion criteria have been analyzed by a clinician in order to highlight and extract one or more concepts for pairing. These criteria may map to one or more interface terminology concepts or groups. Likewise, the interface terminology concepts may map to standards, i.e., administrative, clinical, and/or reference terminology entries with respective codes.

Various interface terminology elements may be related to one another semantically, while, from an architecture standpoint, they may stand alone and may not be related in a formal manner, e.g., they may not be hierarchically related. In one case, however, each interface terminology element may map to a reference terminology code set element such as a SNOMED code set element. Those reference terminology elements may be hierarchically or otherwise formally grouped, and those groupings may be leveraged to generate groupings among multiple interface terminology elements. As discussed in greater detail below, once the clinical trial information and the EHR records are mapped to elements of the interface terminology, those elements and the mappings among elements may be used to determine suitable matches between the clinical trial information and those EHR records. The determining step then may be iterated in order to determine suitable matches for each clinical term.

It surprisingly has been found that more accurate results, i.e., better matches to potential candidates, can be achieved by delineating the mapping step into two substeps: 1) structuring the data, and then 2) coding it. Within the coding subset, it also was determined that more accurate results were obtained when clinical trial criteria were mapped to groups based off the external, e.g., reference, terminology elements, rather than directly to interface terminology elements themselves.

Data structuring may involve parsing uncoded text into categories or domains and then mapping parsed portions of the text to respective concepts or descriptions within those categories or domains. In the medical records context, exemplary domains may include problems, plans, procedures, history, medications, allergies, lab results, past diagnosis, past medications, surgical history, etc. Each domain may have its own database or may be structured in a table within a database. Alternatively, the data may be aggregated in one or more databases without formal arrangement but with entries having flags to denote how it is parsed. This type of structuring may apply to both EHR data and to tagged clinical trial requirements. In addition, with regard to the clinical trial requirements specifically, data structuring may include delineating certain data as pertaining to an inclusion or exclusion criterion.

Conversely, data grouping may involve arranging various interface terminology concepts according to the requirements for each clinical trial, adding specificity and accuracy to queries. Within the database schema, a group may be represented as a token or single variable, and concepts within the group may be represented as an array that is mapped to that token. In one example, that mapping is performed through a SQL line of code that indicates what lexical (descriptions) within each concept are a match.

In one aspect, groups may be created manually based off a clinician's or other user's determination that the concepts underlying a group belong together based on those clinical trial requirements.

In short, data structuring may relate to the relationship between concepts in the context of a terminology schema, whereas data grouping may relate to the relationship between concepts in the context of the trial to which they relate.

The distinction between mapping directly to an interface terminology concept and/or its underlying reference terminology concepts versus building and then mapping to a group is depicted in FIGS. 4-7.

Figure 4:
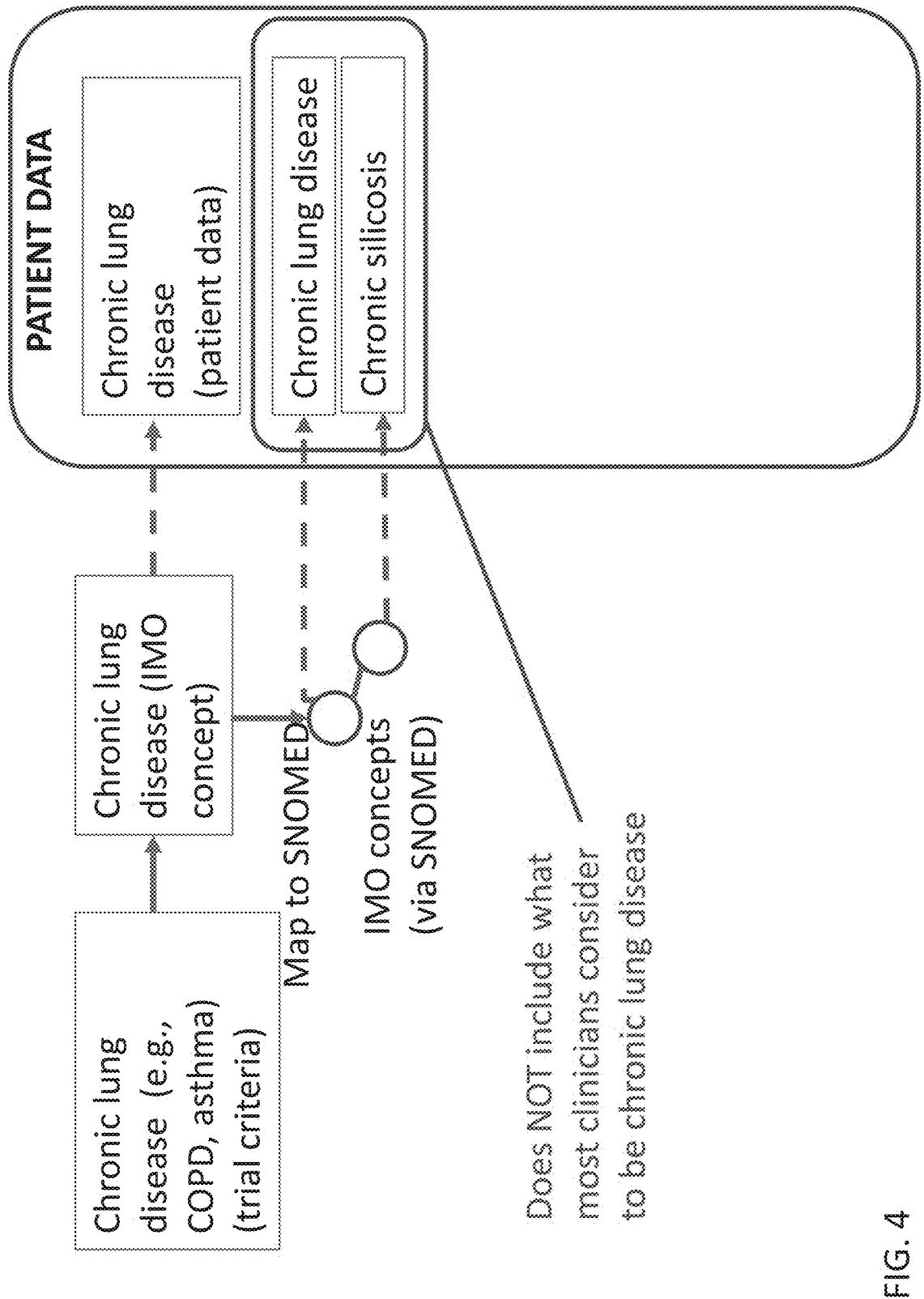
FIG. 4 is a depiction of a workflow mapping a phrase to an interface terminology concept and its underlying reference terminology concepts.

In FIG. 4, the far-left box represents exemplary text found in a database entry for a clinical trial. Proceeding to the next box, that text is mapped to a base interface terminology concept, which in turn is mapped to a corresponding reference (e.g., SNOMED) terminology entry. Using the reference terminology hierarchy as shown beneath that base interface terminology concept, other interface (e.g., IMO) terminology concepts are mapped as related to the base interface terminology element. In this instance, patient data, as represented by the box at the far right, may be searched, and matches may returned when that data includes mappings to the base or additional interface terminology concepts.

In this scheme, exact matches may be returned, which may result in identifying patients with those exact matches in their EHRs. At the same time, however, modeling in this way also may retrieve records for patients whose EHRs include the other mapped concepts. In those cases, although results may be returned, those results may not be as useful to the clinicians organizing the trial, as they may not semantically represent concepts within the parent concept.

Taken to another extreme, it may be the case that an exact interface terminology map may not match semantically with the criteria set forth in the trial summary. For example, as seen in FIG. 4, the problem concepts "chronic lung disease" and "chronic silicosis" may map to the base problem concept "chronic lung disease" due to their relationship through the administrative code mappings, but neither those problem concepts nor the base problem concept may semantically mean "chronic lung disease" in the eyes of most clinicians, generally, or the clinicians seeking participants for a trial, specifically.

Figure 5:
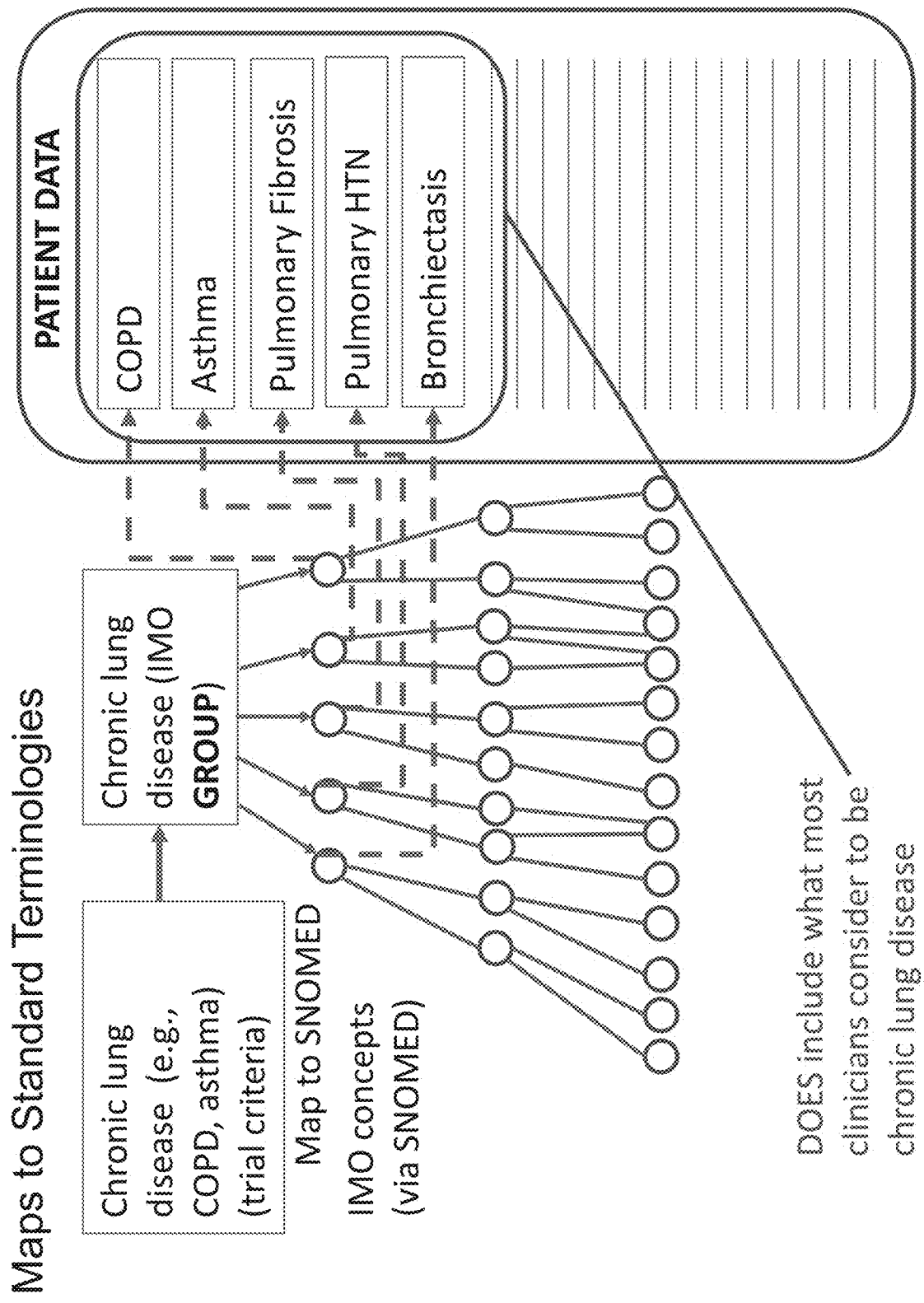
FIG. 5 is a depiction of a workflow mapping a phrase to an interface terminology-guided group and its underlying reference terminology and interface terminology concepts.

Turning now to FIG. 5, the present system and method incorporating interface terminology grouping is depicted. In this example, the same clinical trial data is evaluated, this time for its semantic meaning. For example, a clinician may review the clinical trial data and determine what concepts the clinical trial seeks to encompass. Part of this process may be carried out by a computer, e.g., evaluating the data against the interface terminology for exact matches, alternatives based on synonyms, etc., after which the potential candidates are presented to a reviewer to determine their relevance. The reviewer may analyze the potential candidates and apply his or her own technical knowledge to create a list of interface terminology concepts that are related semantically to the clinical trial concepts. Those interface terminology concepts then are mapped to corresponding reference terminology concepts, which, as in the previous example, are mapped via their hierarchical relationships. This reference terminology mapping is depicted by the modified tree structure in the center of FIG. 5 ("modified," because the reference terminology may permit a child to have one or multiple parents and/or a parent to have one or multiple children). Additionally, since parent and child reference terminology elements are mapped to corresponding interface terminology elements, those corresponding interface terminology elements eventually may be compared against the patient EHR data when attempting to find matches.

Figure 6:
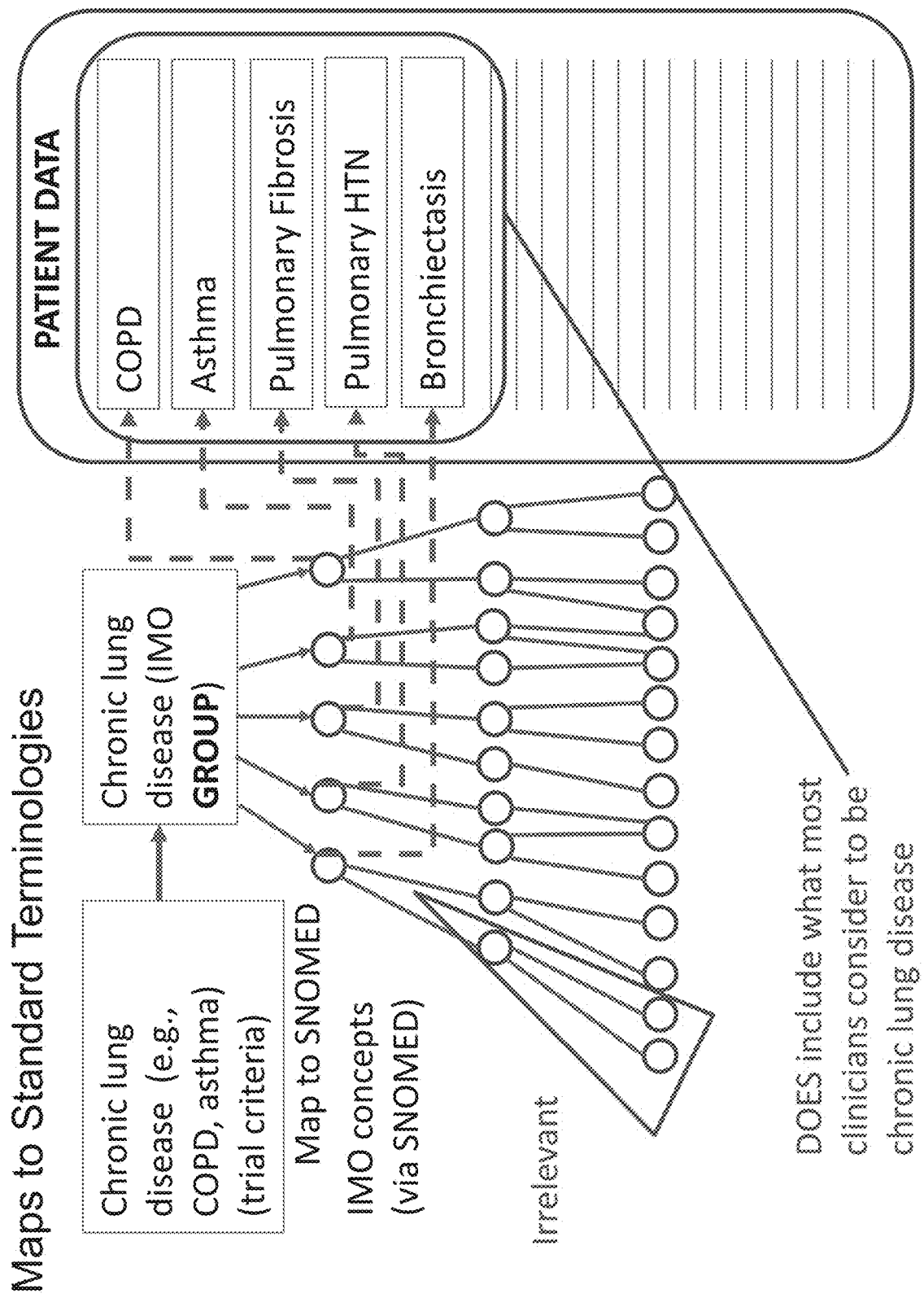
FIG. 6 is a depiction of the workflow of FIG. 5, highlighting concepts determined not to belong to part of the interface terminology-guided group.
Figure 7:
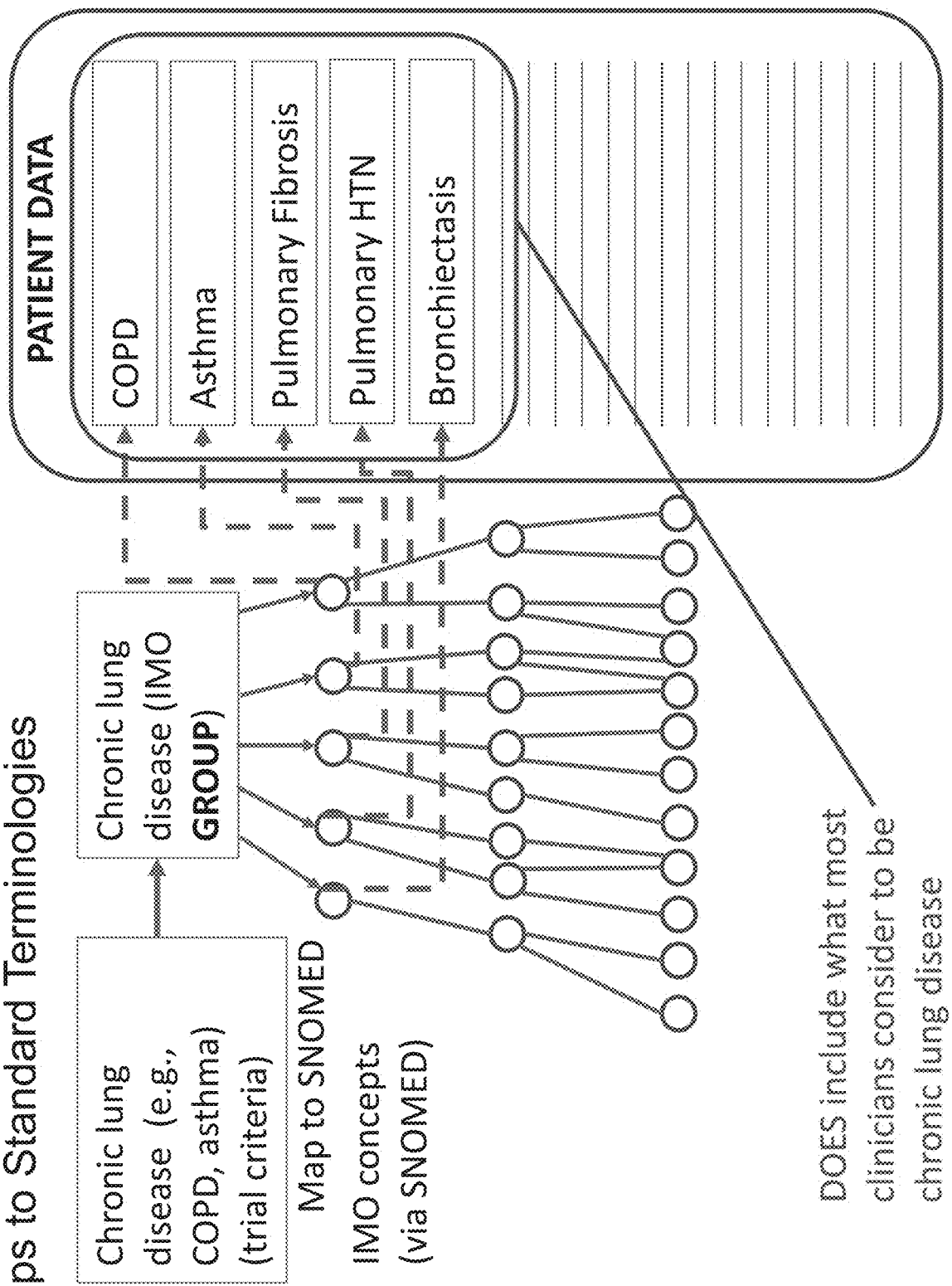
FIG. 7 is a depiction of the workflow of FIG. 6, eliminating the highlighted concepts.

FIGS. 6 and 7 illustrate that, even when groups are implemented, not all reference terminology hierarchical elements (and, via mappings, not all interface terminology elements) within a data structure may be desired. For example, in FIG. 6, the left-most branches enclosed by the triangle may represent concepts that are not desired to be search parameters but that depend hierarchically (using the reference terminology hierarchy) from a desired concept. As seen in FIG. 7, these concepts then may be omitted from the group, leading to more accurate search parameters.

As mentioned above, the group that was created for this example may be specific to the clinical trial to which it pertains, based on the semantic understanding of the trial criteria. Thus, in another instance, a separate clinical trial may refer to "chronic lung disease" as an inclusion or exclusion criterion, but that phrase may mean something different semantically in the context of that separate trial. Thus, the resulting group that is created may include different interface terminology concepts than in this example, in order to account for that different context.

A model statement may include multiple parts. In one example, a model statement may include a first part in which the system receives a selection of one or more interface terminology concepts and corresponding domain values or "keys." A domain key may include, e.g., an interface terminology code representing that interface terminology concept. The model statement also may include a second part in which the system is instructed to analyze a plurality of patient EHR database records and select potential trial participants based on inclusion or exclusion of those values.

For example, for a given trial study, the model statement may include the interface terminology concepts mapping to the inclusion criteria, while also including the interface terminology concepts mapping to any exclusion criteria. In this example, the second part of the model statement may include a complex Boolean query for all medical concepts, e.g., with inclusion criteria connected by an "AND" connector, and exclusion criteria connected by a "NOT" connector.

In one aspect, inclusion and exclusion criteria as mapped to interface terminology elements are analyzed for exact matches of those mappings with EHR data. In another aspect, the inclusion and exclusion criteria as mapped to interface terminology elements are analyzed for matches with EHR data within the groups to which those criteria were assigned.

Key Inclusion Criteria Considerations

Figure 8:
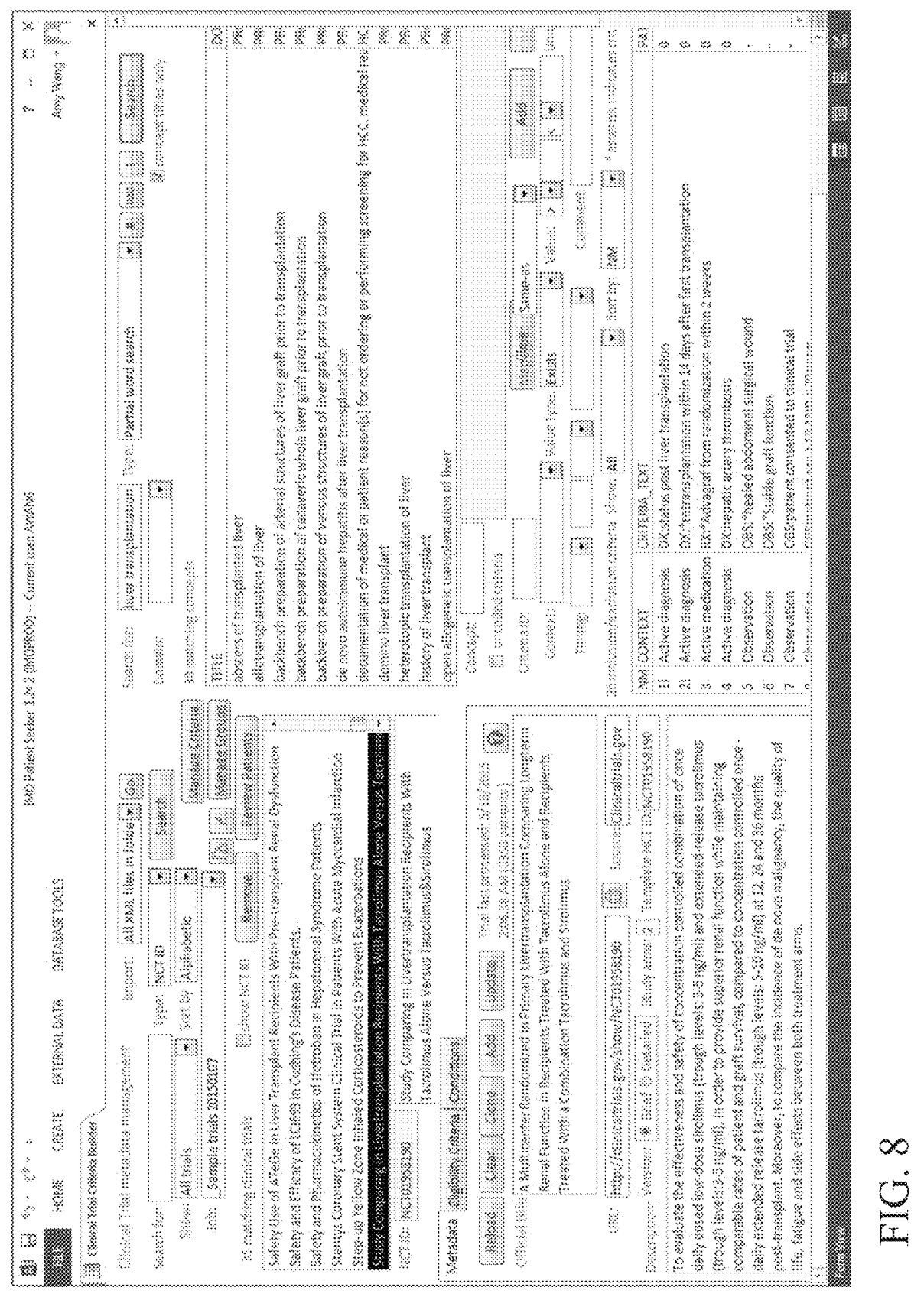

As discussed above, one or more of the trial studies may have at least one key associated with them, and multiple trials may have an expanded key with another inclusion criterion on board. In one example, the key is the primary diagnosis used to collect the first set of patient data. At the same time, the key may be represented by a single interface terminology concept. Preferably, the key is the first inclusion criterion from which all trial requirement criteria sets are built. FIG. 8 depicts an example of a user interface which, in part, may help determine the effect of choosing one key versus another, since, as seen in that figure, inputting a search query in the upper right yields a list of all potential trials with that term, as well as a list of other potential concepts that may be grouped along with the search term.

Key selection may significantly affect the ultimate success of a query. This concept or set of concepts must be data set driven to take advantage of where most of the patients' data resides to capture the correct and broadest net for the first set. The key concept or concept set preferably casts the widest possible net in any given data set, such that the concept(s) chosen may not have the best or most closely matching lexical description of what is required.

It may be rare that a trial has only one or two inclusion criteria, such that it is possible to build many varied queries that may return vastly different results, depending on the choice of key selection. Additionally, data derived from one population, e.g., an ambulatory care population, may exhibit disparate characteristics as compared to data captured from a second population, e.g., inpatient hospital data. Thus, the choice of EHR data source for analysis, or at least for initial analysis, is another aspect of data driven concept choices that is considered for optimum results when searching for and choosing key criteria.

In another aspect, it may be important to rule potential candidates out of a study, such that the key selection and/or one or more subsequent selections may be exclusion criteria.

Key concepts or concept sets should retrieve what would be expected from that particular patient population. If they do not, then the key choice preferably is reexamined and mined for content that may be mapped to a larger set of patient data that meets expectations.

The power in building groups may be to maximize inclusion criteria wherever appropriate and to minimize the use of exclusion criteria until control is gained over seeing how patient coding and subsequent counts start to produce reliable, reproducible results with inclusion sets.

In one aspect, a goal would be to get a plurality of inclusion criteria, e.g., about 3 criteria, per trial and patient age/gender limitations to provide a reasonable first set that seems right size for any given data set. Additional inclusion criteria may be employed to lessen set noise from larger sets, which may be preferable to employing exclusion criteria early on in the iterative process.

Identifying Potential Participants

The system creates model statements, e.g., SQL statements, that will select the correct data from a selected database quickly. The method then may include executing those statements and applying conditions, e.g., Boolean conditions (AND, OR, NOT), to the inclusion and exclusion of potential candidates. The method further may include repeating one or both of these steps in one or more other databases or database environments that may contain records for additional patients. Returning to FIG. 2, a summary of this method step is depicted in which patient EHR data from multiple sources is searched and then compared against structured, codified data representing inclusion and exclusion criteria from one or more trials in order to find pools of patients best suited to those trials.

By way of example, a clinical trial may include the following free text as a description of its inclusion criteria:

Symptoms of an AMI with one of the following 3 symptoms: ST elevation>=1 mm in >=2 contiguous leads or new left bundle branch block, or true posterior MI with ST depression of >=1 mm in >=2 contiguous anterior leads.

In one instance, the concept "acute myocardial infarction" may be assigned to be the "key," since AMI in this context refers to acute myocardial infarction. Alternatively, since the focus is on symptoms and not the acute myocardial infarction itself, it may be possible to exclude or at lease minimize that feature and build a query focusing on the symptoms (Sx) as potential diagnoses (DX). For example, the previous statement may be parsed as:

1. Obs–Age>=18
2. Dx–ST elevation>=1 mm in >=2 contiguous leads
3. Dx–new left bundle branch block
4. true posterior MI with ST depression of >=1 mm in >=2 contiguous anterior leads.

Each element then may be structured by applying the most accurate interface terminology concepts or descriptions to that element. Once this statement is structured with mappings to respective interface terminology elements, the query may be generated as:

1 and (2 or 3 or 4), where 1 is a previous/key concept.

A query generated in this way would represent that any of the 3 Sx of the AMI (and, by extension, the interface terminology concept that maps to each of those symptoms) would need to be present, while leaving the AMI concept itself out of consideration for matching.

Value-Based Criteria Considerations

The method as heretofore described primarily may be used to determine the presence or absence of inclusion and exclusion criteria in one or more EHR records. In another aspect, the method may be applied to find value-based criteria, e.g., age values or ranges, cholesterol ranges, other results in the lab results domain, etc. In that aspect, interface terminology concepts may be created for the variable being assessed, where the new concepts correspond to different possible values or ranges. It is possible that these values do not correspond to any reference terminology entities other than a base entity, e.g., hyperlipidemia, rather than a certain cholesterol range. In that case, the system may benefit by avoiding the formation of a group surrounding the variable or, alternatively, by combining a grouping function to determine the base variable with a concept-based comparison in order to determine the range or specific value being sought.

Medication Coding Considerations

At present, there is no U.S. or international medication standard to identify drug classes, and medication queries may not recognize any reference terminology (e.g., SNOMED or National Drug File, i.e., "NDF-RT") coding. It is possible, however, to harvest active U.S. drug standard content from a clinical terminology such as RxNorm and link it to medication classes from NDF-RT using new RxClass files for Anatomical Therapeutic Chemical ("ATC") Classification and NDF-RT linked to RxNorm ingredients. In order to get complete retrieval using RxNorm, the following term types may be utilized, i.e.: IN (Ingredient), BN (Brand Name), SCD (Semantic Clinical Drug), SBD (Semantic Branded Drug), GPCK (Generic Pack, e.g., for blister packs or ordered drug dosing), and/or BPCK (Brand Pack).

Additionally, in order to increase the potential of returning a pool of satisfactory candidates when using data from a medication domain, one example is to have the Medispan lexical strings identified in SPL (Structured Product Labeling, i.e., electronic data replacing hard package inserts) data that is linked to RxNorm data. Those would give exact RxCui values for the Medispan lexicals (i.e., granular data used to identify what the medication data is) that the data contains. RxClass data should be similar in design and some content.

Temporal Issues:

In still another aspect, one or more trials may have issues that qualify temporal aspects, e.g.:

"The subject requires multivessel PCI at time of index procedure or any staged procedure of the target vessel within 9 months or any non-target vessel within 30 days post-procedure."

In this example, the "within 30 days post-procedure" criterion may not be represented adequately by reference to an interface terminology element directly or, indirectly, to a reference terminology element. Thus, in order to account for this criterion, the system may refer to another criterion, e.g., "multivessel PCI," as the key and then analyze the metadata associated with multiple EHR records to determine when a corresponding reference or interface terminology record was input into those records.

Using Coding Resources to Fulfill Inclusion Criteria Shortcomings

Although mapping to an interface terminology has been described to this point with reference to a reference terminology, other mappings are possible, and experience suggests using whatever resources are available for finding the best concepts embedded in a given patient data set. Thus, the method may include building larger search sets of content from ICD 9 or ICD 10, which require many of the same skills and, therefore, similar codes, for Meaningful Use (Stage 2).

In one aspect, additional inclusion criteria and/or additional terminology mappings may be used to overcome false hits from broader search sets. An example would be building a set for a trial that evaluates limb perfusion, where the query is based on ICD 9 and 10 content including granular content for right and left limbs, since the laterality is coded when billed. In that example, relying solely on the reference terminology (e.g., SNOMED) to build a group may maintain ambiguity, since the reference terminology may not specify left or right in that specific settings.

Example

A database containing approximately twenty years of EHR data for 2.4 million anonymized ambulatory and specialty care patients was tagged with an interface terminology. The data types included full EHR records, thereby including problem/diagnosis, medication, procedure (surgical history), and lab results data types/domains (although the labs were not used as part of this example).

Initially, trial summaries having between 50 and 150 query terms (inclusion and exclusion criteria, along with other identifying factors) were analyzed using all of those possible criteria. In each case, this process yielded 0 matching results from the 2.4 million candidates, indicating the need to broaden the search criteria by reducing the number of query terms being used.

It was found that progressing from the opposite end of the spectrum, i.e., selecting a key criterion and then iteratively generating subsequent queries by adding one or more additional criteria yielded the best results, because the user could pare the subset down to more reasonable numbers while, at the same time, focusing on the criteria that he or she may have deemed most significant.

Alternative Workflow

Figure 9:
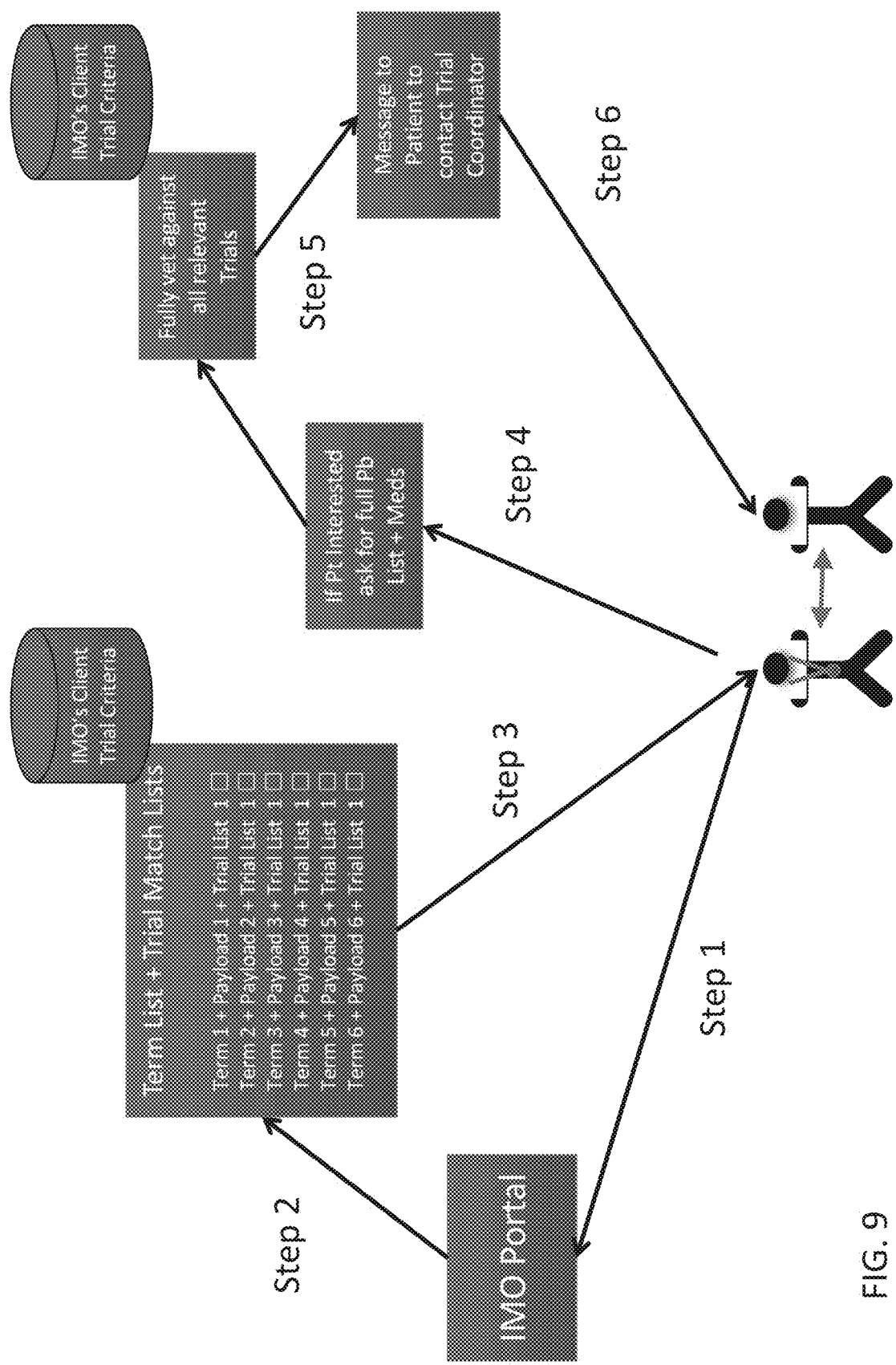
FIG. 9 is a depiction of an alternate workflow.

Whereas much of what has been described to this point may be viewed as a retrospective workflow, inasmuch as the patient electronic health records and clinical trial data already exist, and the method seeks to find one or more patients that match with the clinical trial requirements, FIG. 9 depicts an alternative workflow that may take place between, e.g., a physician and a patient during a care encounter in order to determine if that specific patient is a match for one or more existing studies. In this example, at step 1, the physician or other user may input one or more terms into the patients electronic health record or, alternatively, directly into the system itself. Those terms may be interface terminology descriptions or may map to interface terminology descriptions, e.g., using a method such as the one found in the commonly-assigned U.S. Publication 2014/0122117, titled "Method and System for Concept-Based Terminology Management."

At step 2, the physician or the system then may select one or more of the entered or mapped interface terminology descriptions and, by extension, their interface terminology concepts, against one or more databases of clinical trial criteria to determine which, if any, clinical trials potentially may be a match for the patient's condition. Using the methodology described above, including the selection of key values and/or groupings of the patient's interface terminology concepts, the system may return a list of one or more matching trials in step 3.

At step 4, the patient and/or physician may review the returned list to determine if any of the trials are appealing and, if so, the physician may request fuller information on the resulting trial(s). Because fewer than all of the inclusion and exclusion criteria may have been used to generate the initial matches of step 3, the system or the physician may vet the remaining inclusion and exclusion criteria of the interested trials at step 5. At step 6, the system then may provide contact information for the coordinators of the resulting trials in order for the patient to contact those coordinators and express interest in the study. Alternatively, the patient may consent to the system providing the patient's contact information directly to the coordinator for the selected trial(s) in order for the coordinator(s) to contact the patient directly.

Alternative Use

In addition to identifying potential patients to participate in clinical trials, the present system and method may be employed to identify potential geographical hotspots relating to one or more conditions or to analyze the spread of those conditions. For example, the present system and method may rely on an analysis of EHR data to identify outbreaks of a disease in order to more quickly and efficiently allocate resources for containment and/or treatment.

Figure 10:
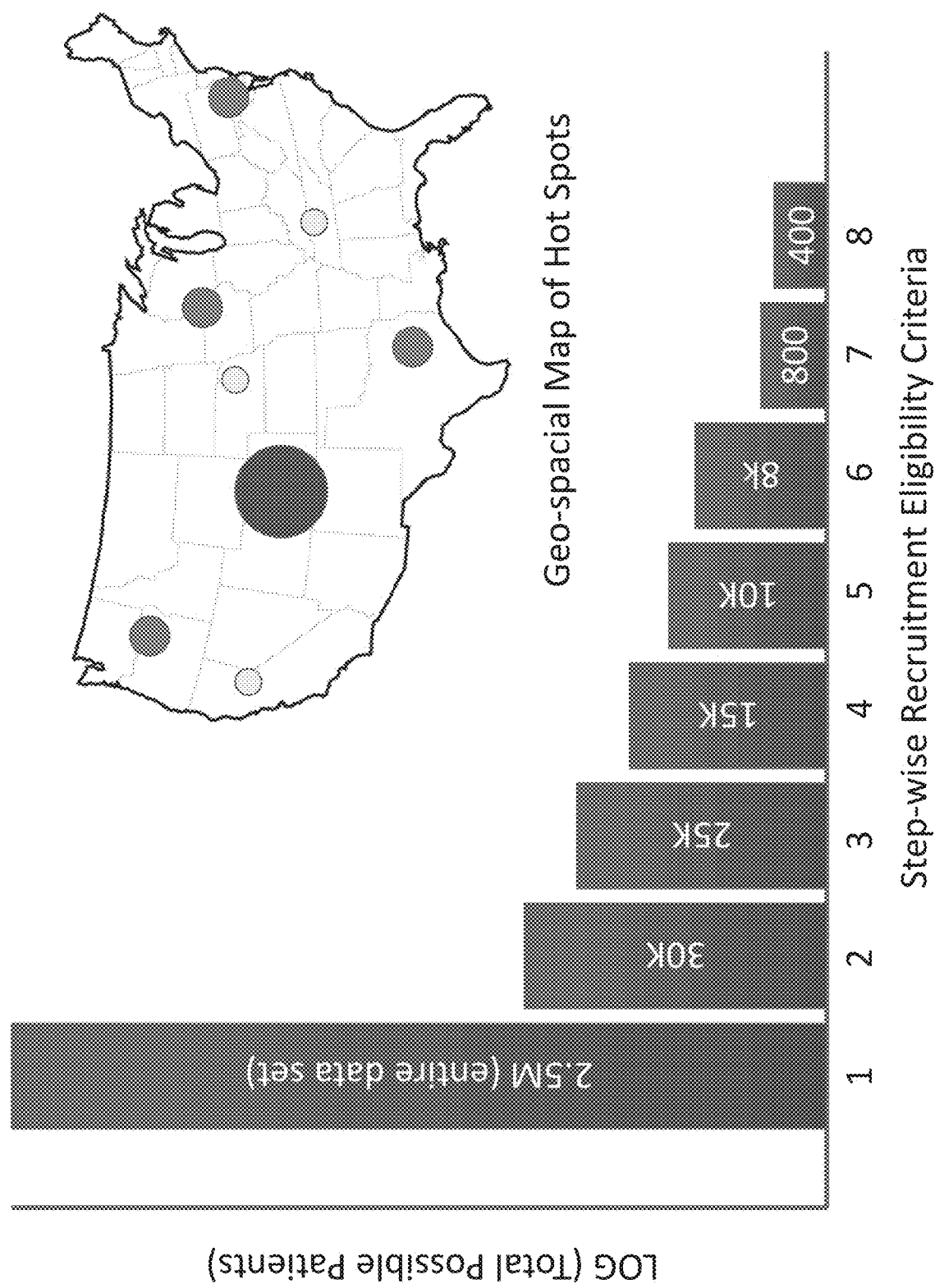
FIG. 10 is a depiction of an alternative use of the present method, including identifying patients matching an increasing number of eligibility criteria and a graphic depiction of clusters of patients meeting those criteria.

Specifically, as represented in FIG. 10, the iterative process of the present method may permit a use to focus in on a group of patients that potentially may be infected with a disease, based on an analysis of symptoms or problems listed in their medical records. For example, adding a first symptom (e.g., fever) may decrease the potential pool from the entire data set to several tens of thousands of patients. Adding progressively more factors may have a corresponding effect on the reduction of potential patients until a certain user-desired data set it achieved. From there, it may be possible to further analyze the data set to see if there are any similarities among the patients, e.g., they all present symptoms around generally the same time period, they are clustered in one or more geographic locations, etc.

By looking at the data generally at the present time, the system may present the user with generally the current state of an outbreak. Similarly, by correlating each patient's EHR listing of symptoms with the date(s) of entry, the system may be able to roughly backtrack the spread of a disease, thereby helping to determine its source and the speed at which it spreads. In one example, the patient EHR data may include location identification information such as a zip code or full home address. The system then may be configured to retrieve that location identification information to plot a heat map or other graphical depiction of the patients matching the requested criteria.

System Configuration

The method may be executed by a system including a warehouse such as the EPIC ENTERPRISE warehouse, which may be built upon a database, such as a relational database and, more specifically, upon an Oracle or Microsoft SQL Server relational database. In an alternative aspect, data within the warehouse may be committed to a Cache database, which may be a hierarchical database providing for fast data storage and retrieval but relatively slower reporting needs such as data aggregation. In still another aspect, the method may be executed by a system employing a database such as an EPIC CLARITY database.

Searches may be formed and executed in one of various formats, and one preferred format is to build and execute the searches as SQL statements. The searching procedure also preferably filters results using inclusion and exclusion criteria hardcoded in the database for all valid Boolean conditions (AND, OR and NOT).

In one aspect, the SQL statement may execute a series of steps, e.g.:

1) Retrieve all the "keys" from a database storing each of the interface terminology concepts using the views combined with the criteria information from one or more tables storing the clinical trials data. This data may be stored in a separate table in the database and may include data representing a patient ID, a criteria ID, and a key value.

2) Parse the inclusion criteria to find the first "stand-alone" criterion. In this context, "first" may not necessarily refer to the first criterion listed but rather may refer to the criterion that a clinician believes is the most significant with regard to identifying potential participants. The computer system then evaluates the database of patient information for a match to this stand-along criterion, copying or linking relevant patient data to another database table to form a primary patient "universe." The information stored in the table may include data representing a patient ID and concept ID.

3) Iterate the process with additional inclusion and exclusion criteria and update the latter table with that additional data using the same format as the previous step. At this stage, the iterations may be independent of one another, such that new potential participants are identified if they match a subsequent criterion, even if they do not match an earlier one.

4) The Boolean logic may be unfolded and analyzed, i.e., interpreted against the patients and their concepts, using an XML or similar function. Results may be written back to another relational table comprising all patient IDs that fully meet that Boolean condition. The XML function may retrieve and transport data from the database, structuring or otherwise breaking down data into smaller pieces than may be possible if solely SQL statements were used. As the number of inclusion and/or exclusion criteria increases, a pure SQL statement may become cumbersome or unwieldy, thereby hampering system performance and increasing processing time necessary to return results. It surprisingly was found that the inclusion of XML functions to carry out the Boolean analysis improved system performance and reduced processing time, despite the need for the system to perform the additional XML function calls.

In one aspect, data may be retrieved from the relational database and converted to an XML data format, e.g., using the XMLQuery function in XQuery. Once extracted from the relational database, another function, e.g., again in XQuery, may be used to execute the Boolean analysis. Results then may be converted back to a native (e.g., relational) format, e.g., by using an XML Table function in order to introduce those results back into the relational database or into a separate relational database. Alternatively, the results may be left structured as XML data for use by the system and/or for storage, e.g., in a file system, an object-oriented database, a special-purpose/semi-structured system, or in a relational database.

In an alternative aspect, the third and fourth steps may be combined such that the addition of other al criteria are being added, updating the table may involve deleting rows, as irrelevant patients (i.e., those matching fewer than all criteria) are removed from the pool. In either case, the system also may post the number of prospective patients/participants to the user interface in order to provide the user with a visual indicator of the effects of the selections.

The system may be accessible as a web-hosted service, preferably presenting the user with a thin client with which to access the system, although a thick client implementation also is possible. Patient data preferably is pre-indexed, speeding up the fourth step and permitting scalability of the system as the number of concepts and patients increases.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

We claim:

1. A method for identifying potential clinical trial participants, comprising:
   (a) receiving, by a computer, a data file including data pertaining to a clinical trial, the data including at least one of an inclusion criterion and an exclusion criterion;
   (b) determining a key concept of an interface terminology ontology pertaining semantically to the data, the interface terminology ontology comprising a plurality of concepts with corresponding codes;
   (c) identifying one or more entries of a reference or administrative code set relating to the key concept in the context of the clinical trial, the reference or administrative code set comprising a plurality of entries with corresponding codes;
   (d) mapping, using a computer, one or more interface terminology concepts to the one or more reference or administrative code set entries;
   (e) analyzing, using the computer, a first database of anonymized patient electronic health record information from a first institution for first patients having a first match to the key concept if the key concept pertains to an inclusion criterion or no first match to the key concept if the key concept pertains to an exclusion criterion;
   (f) analyzing, using the computer, a second database of anonymized patient electronic health record information from a second, separate institution for second patients having a second match to the key concept if the key concept pertains to an inclusion criterion or no second match to the key concept if the key concept pertains to an exclusion criterion;
   (g) aggregating the first and second patients for reporting to a user; and
   (h) returning the aggregated first and second patients to the user,
   wherein the first database stores patient information from a first electronic health record provider and the second database stores patient information from a second, distinct electronic health record provider,
   wherein the first and second matches are represented by patient information that is stored in different formats in the first and second databases and that pertains an inclusion criterion or that pertains to an exclusion criterion, and
   wherein the first and second matches each comprise a direct match to the key concept or a match to one of the one or more interface terminology concepts mapped to the one or more reference or administrative code set entries.

2. The method of claim 1, further comprising determining one or more additional concepts of the interface terminology ontology pertaining to the data.

3. The method of claim 2,
   wherein each analyzing step comprises building a query including the key concept and the one or more additional concepts and comparing the respective database of patient electronic health record information against the query.

4. The method of claim 3,
   wherein the query is structured using Boolean logic.

5. The method of claim 3,
   wherein the query comprises a SQL statement including a call to an XML function that executes one or more Boolean operators acting on the at least one of an inclusion criterion and an exclusion criterion.

6. A method for identifying potential clinical trial participants, comprising:
   receiving, by a computer, a data file including data pertaining to a clinical trial, the data including at least one of an inclusion criterion and an exclusion criterion;
   mapping, using a computer, one or more concepts of an interface terminology ontology to each of the at least one inclusion criterion and the at least one exclusion criterion, the interface terminology ontology comprising a plurality of concepts with corresponding codes;
   determining a key concept of the interface terminology ontology pertaining to the data;
   identifying one or more concepts of the interface terminology ontology relating to the key concept in the context of the clinical trial;
   analyzing, using the computer, a database of patient electronic health record information for a match to the key concept or the one or more interface terminology concepts relating to the key concept; and
   presenting, to a user, information relating to a patient to which the match pertains via a graphical user interface generated by the computer,
   wherein the match and the key concept or the one or more interface terminology concepts relating to the key concept are stored in different formats and pertain to the at least one inclusion criterion or the at least one exclusion criterion,
   wherein the analyzing step comprises building a query including the key concept and the one or more interface terminology concepts relating to the key concept and comparing the database of patient electronic health record information against the query, and
   wherein the query comprises a SQL statement including a call to an XML function that executes one or more Boolean operators acting on the at least one of an inclusion criterion and an exclusion criterion.

7. The method of claim 6, further comprising:
   determining one or more additional concepts of the interface terminology ontology pertaining to the data;
   revising the query to include the one or more additional concepts; and
   iterating the analyzing step by comparing the database of patient electronic health record information against the revised query.

8. The method of claim 6, further comprising:
   determining one or more additional concepts of the interface terminology ontology pertaining to the data.

9. The method of claim 7,
   wherein the analyzing step comprises building a query including the key concept and the one or more additional concepts of the interface terminology ontology and comparing the database of patient electronic health record information against the query.

10. The method of claim 6, wherein the key concept pertains to an inclusion criterion of the clinical trial.

11. The method of claim 6, wherein the key concept pertains to an exclusion criterion of the clinical trial.

12. A method for identifying potential clinical trial participants, comprising:
   (a) receiving, by a computer, a data file including data pertaining to a clinical trial, the data including at least one inclusion criterion and at least one exclusion criterion;
   (b) mapping, using a computer, one or more concepts of an interface terminology ontology to each of the at least one inclusion criterion and the at least one exclusion criterion, the interface terminology ontology comprising a plurality of concepts with corresponding codes;
   (c) mapping, using a computer, elements of a database of patient electronic health record information to one or more interface terminology ontology elements;
   (d) building a query including at least one of the at least one inclusion criterion and the at least one exclusion criterion, wherein the query is a SQL statement including a call to an XML function that executes one or more Boolean operators acting on the at least one inclusion criterion and the at least one exclusion criterion;
   (e) determining, by a computer, which elements of the interface terminology ontology map to the at least one inclusion criterion and the at least one exclusion criterion;
   (f) analyzing, by the computer, the elements of the database of patient electronic health record information for a match to the determined elements of the interface terminology ontology; and
   (g) presenting, to a user, information relating to a patient to which the match pertains via a graphical user interface generated by the computer,
   wherein multiple matching elements are stored in the database in different formats and pertain to the at least one inclusion criterion or the at least one exclusion criterion.

13. The method of claim 12, wherein step (a) includes building a group comprising one of the one or more interface terminology ontology concepts and one or more additional interface terminology ontology concepts, where the concepts are related in the context of the clinical trial.

14. The method of claim 13, wherein the one or more additional interface terminology ontology concepts are mapped to further interface terminology ontology elements using a structured relationship defined by a reference code set mapped to the interface terminology elements, the reference code set comprising a plurality of entries with corresponding codes.

15. The method of claim 12, wherein the building step comprises building a query comprising a plurality of inclusion criteria, wherein the query is structured using Boolean logic.

* * * * *